United States Patent
Gagnon et al.

(10) Patent No.: US 9,994,611 B2
(45) Date of Patent: *Jun. 12, 2018

(54) CHROMATOGRAPHIC PURIFICATION OF ANTIBODIES FROM CHROMATIN-DEFICIENT CELL CULTURE HARVESTS

(71) Applicant: AGENCY FOR SCIENCE, TECHNOLOGY AND RESEARCH, Connexis (SG)

(72) Inventors: Peter Stanley Gagnon, Centros (SG); Tze Yang Lee, Centros (SG)

(73) Assignee: AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 202 days.

This patent is subject to a terminal disclaimer.

(21) Appl. No.: 14/769,098

(22) PCT Filed: Feb. 27, 2014

(86) PCT No.: PCT/SG2014/000088
§ 371 (c)(1),
(2) Date: Aug. 19, 2015

(87) PCT Pub. No.: WO2014/133459
PCT Pub. Date: Sep. 4, 2014

(65) Prior Publication Data
US 2016/0009762 A1   Jan. 14, 2016

Related U.S. Application Data

(60) Provisional application No. 61/771,021, filed on Feb. 28, 2013.

(51) Int. Cl.
| | | |
|---|---|---|
| C07K 1/30 | (2006.01) | |
| C07K 1/36 | (2006.01) | |
| C07K 1/16 | (2006.01) | |
| C07K 16/32 | (2006.01) | |
| C07K 1/32 | (2006.01) | |

(52) U.S. Cl.
CPC .................. *C07K 1/36* (2013.01); *C07K 1/30* (2013.01); *C07K 1/32* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 5,164,487 A | 11/1992 | Kothe et al. | |
| 7,186,410 B2 * | 3/2007 | Chtourou | C07K 16/065 424/176.1 |
| 2004/0260066 A1 * | 12/2004 | de Leon | C07K 14/765 530/363 |
| 2012/0101262 A1 | 4/2012 | Arunakumari et al. | |
| 2012/0232005 A1 * | 9/2012 | Dasseux | C07K 14/775 514/7.4 |

FOREIGN PATENT DOCUMENTS

| | | |
|---|---|---|
| WO | WO 2004/092393 | 10/2004 |
| WO | WO 2005/073252 | 11/2005 |
| WO | WO 2010/151632 A1 | 12/2010 |
| WO | WO 2010/151632 A8 | 12/2010 |
| WO | WO 2014/123485 | 8/2014 |
| WO | WO 2015/126330 A2 | 8/2015 |
| WO | WO 2015/126330 A3 | 8/2015 |

OTHER PUBLICATIONS

Kuczewsk et al.; "A single-use purification process for the production of a monoclonal antibody produced in a PER.C6 human cell line", Biotechnol. J. 6 (2011) pp. 56-65.
Brodsky et al.; "Caprylic acid precipitation method for impurity reduction: an alternative to conventional chromatography for monoclonal antibody purification", Biotechnol. Bioeng., vol. 109, No. 10, (2012), pp. 2589-2598.
Gan et al.; "Characterization and removal of aggregates formed by nonspecific interaction of IgM monoclonal antibodies with chromatin catabolites during culture production", Journal of Chromatography A, vol. 1291, (2013), pp. 33-40.
Nian et al.; "Void exclusion of antibodies by grafted-ligand porous particle anion exchangers", Journal of Chromatography A, vol. 1282, Mar. 22, 2013, pp. 127-132.
Extended European Search Report dated Sep. 14, 2016 for Appln. 14756552.7.
Bresolin et al., "Adsorption of human serum proteins onto TREN-agarose: Purification of human IgG by negative chromatography", Journal of Chromatography B, 877, (2009), pp. 17-23.
International Search Report dated Aug. 19, 2014 for Appln. No. PCT/SG2014/000088.
Gagnon, "Purification Tools for Monoclonal Antibodies", Validated Biosystems, 1996, pp. 1-269.
English translation of Japanese Office Action dated Nov. 21, 2017 in related application No. 2015-560141.

* cited by examiner

*Primary Examiner* — Daniel E Kolker
*Assistant Examiner* — James L Rogers
(74) *Attorney, Agent, or Firm* — Pillsbury Winthrop Shaw Pittman LLP

(57) ABSTRACT

Methods for the improved purification of antibodies and other proteins from protein preparations including the steps of conditioning the protein preparation by contacting it with multivalent organic ions, then applying the conditioned preparation to an adsorptive chromatography medium.

12 Claims, No Drawings

CHROMATOGRAPHIC PURIFICATION OF ANTIBODIES FROM CHROMATIN-DEFICIENT CELL CULTURE HARVESTS

BACKGROUND

Embodiments disclosed, herein relate to methods for purification of IgG monoclonal antibodies.

Purification of recombinant proteins commonly begins with a so-called primary capture step, in which cells and debris are removed so that the remaining supernatant can be processed by methods that would be hampered or rendered ineffective by the presence of cells and debris. Their removal commonly involves centrifugation and filtration. It sometimes involves the use of membrane or depth filters with anion exchange capabilities, or the addition of anion exchange particles directly to the antibody-containing harvest (Gagnon, P., *Purification Tools for Monoclonal Antibodies, Validated Biosystems, Tucson,* 1996; Kuczewski, M, et al, *Biopharm Int* 23 (3) (2010) 20-25; Kuczewski, M., et al, *Biotechnol. J.,* 6 (2011) 56-65), in all such cases reportedly to reduce levels of host cell proteins (HCP). Brodsky et al (Biotechnol. Bioeng. 109 (2012) 2589-2598) described HCP precipitation by caprylic acid as a precursor of subsequent purification by protein A affinity chromatography. Gan et al (J. Chromatogr. A 1291 (2013) 33-40) employed a different approach of preparing a harvest for subsequent chromatographic purification by specifically targeting a subset of host cell contaminants derived from chromatin, consisting chiefly of histone proteins and DNA. One of those method particularly employed a combination of soluble multivalent organic cations to dissociate aggregates, and insoluble (surface immobilized) multivalent organic ions to remove remaining aggregates and other contaminants. They also described the inclusion of allantoin among the active ingredients to achieve their results.

SUMMARY

In some aspects, embodiments disclosed herein provide methods for the purification of at least one desired monoclonal antibody from an impure preparation in the form of a cell culture harvest, comprising the steps of (i) conditioning the antibody preparation to remove the majority of chromatin by contacting it with soluble and/or insoluble (surface-immobilized) multivalent organic ions then removing solids; (ii) applying the conditioned antibody preparation to an adsorptive chromatography medium that fractionates the desired antibody from undesired contaminants.

DETAILED DESCRIPTION

It has been discovered that in some embodiments the conditioning of an antibody-containing protein preparation by exposure to soluble organic multivalent ions and/or organic multivalent ions immobilized on a solid surface under conditions where the antibody is not bound enhances the subsequent performance of fractionation by protein A to an unexpectedly high degree. By way of illustration, in some embodiments where the organic multivalent ion conditioning step reduces contamination from host proteins by a factor of 30-70%, it can surprisingly increase the ability of a subsequent protein A chromatography step to reduce host protein contamination by up to a factor of nearly 1000-fold. In some embodiments, the methods provides conditioning methods which do not simply aid subsequent purification by reducing the gross contaminant load, but by also particularly removing contaminants that interfere with a subsequent purification step such as a protein A purification step. In some embodiments, the methods surprisingly increases the dynamic binding capacity of protein A affinity columns by 10-20% or more. Without adopting any particular belief or theory, the increased capacity afforded to affinity chromatography media by embodiments disclosed herein may result from the fact these conditioning methods particularly remove large nucleosome-antibody aggregates that bind to the external surface of the particles and prevent the desired antibody from being able to freely enter the pores where most of the intended binding surface area resides. In some embodiments, these conditioning methods may also increase the usage life of the protein A column by preventing its exposure to compounds that potentially foul its surface by non-specific binding thereto. Additionally, these conditioning methods may disproportionately compound the removal of virus. Remarkably, and most surprisingly, the disclosed clarification methods remove interfering substances to such a degree that they also enable adsorptive chromatography methods of lesser purification ability, such as cation exchange, anion exchange, and multimodal methods, to achieve virtually the same purification performance as protein A affinity chromatography. Specifically, the disclosed clarification methods permit all of the chromatography methods named above to reduce host protein contaminants to less than 10 ppm, as measured by commercial host protein ELISA.

It has been discovered that combinations of materials that are chemically antagonistic to one another have the unexpected effect of achieving higher levels of chromatin removal than conditioning methods relying on any one of the materials individually. Combinations of antagonistic materials would be expected to cancel each others' individual effects and result in inferior chromatin reduction, inferior antibody recovery, or both. Instead, the present embodiments provide defined windows within which the materials work synergistically to achieve levels of chromatin reduction and antibody recovery that are substantially beyond the ability of any of the individual components to provide. In addition, experimental results indicate that reactivity curves for each of the components in the combination is distinct from their reactivity curves when used individually. This highlights that the utility of the embodiments disclosed herein could not have been predicted by the known properties or applications of the individual components. In some such embodiments, the components to be combined for conditioning a cell culture harvest particularly include fatty acids containing 7 or 8 or 9 or 10 carbon atoms, and soluble or solid materials bearing a positive charge. They may further include one or more solid or soluble materials that comprise a metal binding functional group. They may further include allantoin. In the methods disclosed herein, the materials are combined in a liquid preparation containing a species of antibody, then after a suitable period of incubation, solids are removed to provide a solution comprising the antibody, absent up to 99% or more of host cell contaminants, with an average IgG recovery of about 90 to about 95%, and a turbidity of less than about 5 NTU (nephelometric turbidity units).

Experimental data document the mutually antagonistic interactions among such components. For example, a cationic (electropositive) component and an anionic (electronegative) component such as a fatty acid should have a strong attraction to one another, and their interaction should tend to reduce the ability of either one to interact with other components of an antibody preparation such as a cell culture harvest. This is indicated by data showing that certain contaminants, such as antibody light chains, are removed by a combination of components at one ratio, but re-appear in the antibody-containing liquid if the proportion of the cationic component is increased. In one particular example, this is believed to occur because a fatty acid bound to a contaminant within a precipitate is more strongly attracted to a cationic solid than it is to the contaminant, so that when the amount of the cationic solid is increased, the fatty acid transfers to that solid, which liberates the contaminant from the precipitate, causing it to re-contaminate the soluble antibody preparation. In another example of mutual antagonism, crystalline allantoin has been shown experimentally to bind more than 99% of the fatty acids in cell culture harvest, indicating a high likelihood that it acts on added fatty acids in a similar manner. This should be expected to reduce the effectiveness of fatty acids added to an antibody-containing cell culture harvest for the purpose of precipitating non-antibody contaminants. To the contrary, this aspect of the methods contribute to effective use of fatty acids at concentrations less than half the levels reported as optimum in the scientific literature. Without ascribing to any particular theory, it may be that fatty acids complexed to undissolved allantoin through hydrogen bonding conserve their native charge, hydrophobicity, and ability to bind contaminants, while the density of the undissolved allantoin enhances their removal by sedimentation. In another example of mutual antagonism, addition of anionic chelating solids—which should be inert to fatty acids—to a mixture of fatty acids and cationic chelating solids, releases contaminants back to the antibody solution that were successfully removed by the already-antagonistic combination of cationic solids and fatty acids. When normally antagonistic components are combined in properly balanced proportions, they create windows within which it is possible to remove contaminants, such as certain antibody fragments, that are not removed effectively by any of the individual components. In many cases, overall purification performance of the disclosed methods exceeds the capabilities of protein A affinity chromatography, which is generally regarded as the highest performing antibody purification method available.

In another such embodiment, the harvest may be conditioned by contact with one or more positively charged surfaces. In another such embodiment, the clarification method involves contacting the desired product preparation with soluble and/or insoluble multivalent organic ions, any one of which may be anionic or cationic, thereby presenting additional examples of inherent antagonism among conditioning components.

In one or more of the preceding embodiments, conditioning the protein preparation with organic multivalent ions comprises contacting the sample with an electropositive organic additive. In some such embodiments, the electropositive organic additive comprises at least one species from the group consisting of ethacridine, methylene blue, cetyl trimethylammonium bromide. In some such embodiments, the concentration of such a species, or aggregate concentration of a combination of species is in the range of 0.001 to 1%, or 0.01 to 0.1%, or 0.02 to 0.05%. In some such embodiments the pH of the preparation may be adjusted up to an alkaline value that does not cause significant reduction of recovery of the desired protein. In one such embodiment where the desired protein is an IgG monoclonal antibody, the pH may be adjusted up to a pH value a half pH unit of the antibody isoelectric point, or more if experimental results indicate that antibody recovery is acceptable, but such adjustments are generally not necessary. To the extent that any pH adjustment is made, a value within 1 pH unit of the protein isoelectric point will suffice, or within 1.5 pH units.

In one or more of the preceding embodiments, conditioning the protein preparation with organic multivalent ions comprises contacting the sample with an electronegative organic additive. In some such embodiments, the electronegative organic additive comprises at least one species from the group consisting of heptanoic acid, heptenoic acid, octanoic acid, octenoic acid, nonanoic acid, nonenoic acid, decanoic acid, methyl blue. In some such embodiments, the concentration of such a species, or total concentration of a combination of species is in the range of 0.001 to 10%, or 0.01 to 1%, or 0.1 to 0.5%. In some such embodiments the pH of the preparation may be adjusted down to an acidic value that does not cause significant reduction of recovery of the desired protein. In some such embodiments, the pH of the preparation may be adjusted to the range of 3.5 to 6.5, 4.0 to 6.0, 4.5 to 5.5, 5.0 to 5.3, 5.15 to 5.25, or 5.2, or another intermediate value.

In one or more of the preceding embodiments, conditioning the protein preparation with organic multivalent ions comprises contacting the sample with undissolved allantoin. In some such embodiments, the added allantoin resident in a protein preparation may amount to about 0.6% to 50%, or 0.7 to 20%, or 0.8 to 10%, or 0.9 to 5%, or 1 to 2%, or an intermediate value. It will be apparent that the smaller the particle size, the greater the surface area per unit of mass, and since the process is mediated at the particle surface, the smaller the average particles size, the greater the efficiency per unit of mass.

In one or more of the preceding embodiments, conditioning the protein preparation with organic multivalent ions comprises contacting the sample with a nonionic or zwitterionic surfactant at a concentration lower than its critical micelle concentration.

In one or more of the preceding embodiments, conditioning of the protein preparation with organic multivalent ions comprises (i) providing a first component which is a first solid substrate having an electronegative surface; (ii) contacting the protein preparation with the first component, wherein the operating conditions substantially prevent the binding of the desired protein to the first component; and (iii) separating the desired protein with a reduced chromatin content from the first component. In some such embodiments, the first electronegative surface may be accompanied by a second electronegative surface.

In one or more of the preceding embodiments, conditioning of the protein preparation with organic multivalent ions comprises (i) providing a first component which is a first solid substrate having an electropositive surface; (ii) contacting the protein preparation with the first component, wherein the operating conditions substantially prevent the binding of the desired protein to the first component; and (iii) separating the desired protein with a reduced chromatin content from the first component. In some such embodiments, the first electropositive surface bears residues of tris(2-aminoethyl)amine. In some such embodiments, the first electropositive surface may be accompanied by a second electropositive surface.

In one or more of the preceding embodiments, conditioning of the protein preparation with organic multivalent ions comprises (i) providing a first component which is a first solid substrate having an electropositive surface; (ii) providing a second component which is a second solid substrate having an electronegative surface; (iii) contacting the protein preparation with the first and second components, wherein the first and second components are configured such that the protein preparation may contact both components simultaneously, wherein the operating conditions substantially prevent the binding of the desired protein to the first or second components; and (iv) separating the desired protein with a reduced chromatin content from the first and second components. In some such embodiments, the first electropositive surface bears residues of tris(2-aminoethyl)amine.

In one or more of the preceding embodiments, conditioning of the protein preparation with organic multivalent ions comprises (i) contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (ii) separating the protein preparation from the at least one surface-bound ligand.

In one or more of the preceding embodiments, a protein preparation already treated with a soluble electropositive or electronegative organic additive and/or a solid surface bearing an electronegative, electropositive, or metal affinity ligand, may be subsequently flowed through a device, the fluid-contact surface of which comprises positive charges.

In one embodiment illustrating application of a chromatin-directed clarification method, allantoin is added to a cell culture harvest in an amount of 1% (v/v). The cell culture may contain cells, or the cells may previously have been removed. Methylene blue is added to a concentration of 0.025% (w/v). Alternatively, ethacridine may be added to a concentration of 0.025%. Alternatively, 0.025% cetyl trimethyl ammonium bromide may be added to a concentration of 0.025%. Alternatively, 0.01% chlorhexidine is added. Alternatively, other electropositive organic additives or combinations thereof may be used. The mixture is then incubated stirring for 2 hours. Particles bearing the electropositive metal affinity ligand tris(2-aminoethyl)amine (TREN) are added in an amount of 2-5% v:v. The mixture is incubated stirring for 4 hours then the solids are removed by any expedient means. The remaining solution containing the desired protein may be optionally flowed through a depth filter bearing positive charges on its fluid contact surface.

In another embodiment illustrating application of a chromatin-directed conditioning method, allantoin is added to a cell culture harvest in an amount of 1% (v/v). The cell culture may contain cells, or the cells may previously have been removed. 0.6% heptanoic acid is added. Alternatively 0.5% heptenoic acid is added. Alternatively 0.4% octanoic acid is added. Alternatively 0.4% octenoic acid is added. Alternatively 0.3% pelargonic (nonanoic) acid is added. Alternatively 0.4% nonenoic acid is added. Alternatively 0.2% caloric acid is added. Alternatively, 0.5% methyl blue is added. Alternatively, a combination of these or other electronegative organic additives may be used. The mixture is then incubated stirring for 2 hours. Particles bearing the electropositive metal affinity ligand tris(2-aminoethyl)amine (TREN) are added in an amount of 2-5% v:v. The mixture is incubated mixing for 4 hours then the solids removed by any expedient method. The remaining solution containing the desired protein may be optionally flowed through a depth filter bearing positive charges on its fluid contact surface.

In another embodiment illustrating application of a chromatin-directed conditioning method, particles bearing a metal affinity ligand, such as an electropositive metal affinity ligand, are added to a cell culture harvest in an amount of 2-5% (v/v). In some such embodiments the electropositive metal affinity ligand is tris(2-aminoethyl)amine (TREN). In some such embodiments the metal affinity ligand is a structural analog of TREN, or multiple of TREN such as a multilayer TREN dendrimer on a particle surface. In some such embodiments, particles bearing ligands that enable them to participate in other chemical interactions are included, with TREN particles or sequentially, including where other particles may be added first. The mixture is incubated mixing for 4 hours then the solids removed by any expedient method. The remaining solution containing the desired protein may be optionally flowed through a depth filter bearing positive charges on its fluid contact surface.

In one or more of the previous embodiments, salt may be added to a conditioning mixture to prevent loss of the desired protein through excessive interactions with a soluble or insoluble multivalent organic ion. In some such embodiments, NaCl may be added to increase conductivity to a level corresponding to about 200 mM, with a rough conductivity equivalent of about 20 mS/cm, for the purpose of preventing an IgM antibody or non-antibody protein from binding to conditioning components. In other such embodiments, the NaCl concentration may be elevated to a greater or lesser degree to accommodate a particular recombinant protein. Appropriate salt concentrations for accommodating any particular protein can be quickly and easily estimated by applying a sample of the desired protein to a cation exchanger or an anion exchanger, eluting them with an increasing salt gradient, determining the conductivity at the center of the desired protein peak, then using that conductivity value for the clarification process.

In some embodiments, methods are provided methods for the purification of at least one desired protein from a protein preparation comprising the steps of (i) conditioning the protein preparation by contacting it with multivalent organic ions; and then (ii) applying the resulting protein preparation to an affinity chromatography medium specific for the desired protein. In some such embodiments, the affinity ligand on the chromatography medium is protein A, or protein G, or immobilized VHH domains, or synthetic analogs of biological chromatography media, or synthetic affinity ligands not modeled on biological affinity ligands.

In some embodiments, methods are provided methods for the purification of at least one desired protein from a protein preparation comprising the steps of (i) conditioning the protein preparation by contacting it with multivalent organic ions; and then (ii) applying the resulting protein preparation to an anion exchange chromatography medium. In certain such embodiments, the anion exchange chromatography medium is a column of packed electropositive particles. In certain such embodiments, the anion exchange column is run in void exclusion mode (Nian et al, J. Chromatogr. A 1282 (2013) 127-132). Such embodiments highlight the surprising nature of the disclosed methods. Anion exchange chromatography has been ignored as an initial purification tool for IgG antibodies because the column becomes severely fouled by binding contaminants from the feed stream. Experimental data show that the contaminants responsible for fouling are almost entirely derived from chromatin, and that their removal endows anion exchange chromatography with the ability to rival the purification performance of protein A affinity chromatography. Anion exchange chromatography in void exclusion mode further enables simultaneous removal of small molecule contaminants and salts, thereby making advance sample equilibration unnecessary.

In some embodiments, methods are provided methods for the purification of at least one desired protein from a protein preparation comprising the steps of (i) conditioning the protein preparation by contacting it with multivalent organic ions; and then (ii) applying the resulting protein preparation to a cation exchange chromatography medium. Experimental data show that cation exchange chromatography performed on cell culture harvest conditioned by the traditional methods of centrifugation and/or filtration typically reduces host protein contamination to 5,000-15,000 ppm. Experimental data show that conditioning of cell culture harvest by the disclosed methods enables cation exchange chromatography to reduce host cell proteins to less than 10 ppm, and in some cases to 1 ppm or less. Another unexpected benefit revealed by experimental data is that chromatin is the contaminating material that fouls cation exchangers and reduces their purification performance. The disclosed conditioning methods particularly eliminate that problem. This solution also applies to multimodal chromatography media employing cation exchange materials with excess hydrophobicity, which following conditioning by the disclosed methods also reduce host protein contamination to 1 ppm.

In some embodiments, methods are provided methods for the purification of at least one desired protein from a protein preparation comprising the steps of (i) conditioning the protein preparation by contacting it with multivalent organic ions; and then (ii) applying the resulting protein preparation to an apatite chromatography medium, such as hydroxyapatite, or fluorapatite, or calcium derivatized versions of either, where the benefits of conditioning the harvest parallel those described for other chromatography media as described above.

In some embodiments, the conditioning of the protein preparation with organic multivalent ions of step (i) comprises contacting the protein preparation with a soluble electropositive organic additive.

In some embodiments, the conditioning of the protein preparation with organic multivalent ions of step (i) comprises providing a first component which is a first solid substrate having an electronegative surface, providing a second component which is a second solid substrate having an electropositive surface, contacting the protein preparation with the first and second components, wherein the first and second components are configured such that the protein preparation may contact both components simultaneously, wherein the operating conditions substantially prevent the binding of the desired protein to the first or second components; and separating the desired protein from the first and second components in a conditioned protein preparation. In certain such embodiments, the conditioning of the protein preparation with organic multivalent ions of step (i) includes, prior to contacting the protein preparation with the first and second components, contacting the protein preparation with a soluble electropositive organic additive. In others, the conditioning of the protein preparation with organic multivalent ions of step (i) includes, during at least a portion of the contacting the protein preparation with the first and second components, contacting the protein preparation with a soluble electropositive organic additive. In certain such embodiments, the conditioning of the protein preparation with organic multivalent ions of step (i) includes, during at least a portion of the contacting the protein preparation with the first and second components, additionally contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and separating the resulting conditioned protein preparation from the at least one surface-bound ligand; wherein when more than one surface-bound ligand is present, each surface-bound ligand is independently either of the same charge or charge neutral.

In some embodiments, the conditioning of the protein preparation with organic multivalent ions of step (i) includes contacting the protein preparation with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and separating the resulting conditioned protein preparation from the at least one surface-bound ligand; wherein when more than one surface-bound ligand is present, each surface-bound ligand is independently either of the same charge or charge neutral. In certain such embodiments, the conditioning of the protein preparation with organic multivalent ions of step (i) includes, prior to contacting the protein preparation with the solid surface comprising at least one surface-bound ligand capable of binding a metal, contacting the protein preparation with a soluble electropositive organic additive; in others, the conditioning of the protein preparation with organic multivalent ions of step (i) includes, during at least a portion of the contacting the protein preparation with the solid surface comprising at least one surface-bound ligand capable of binding a metal, contacting the protein preparation with a soluble electropositive organic additive. In certain such embodiments, the conditioning of the protein preparation with organic multivalent ions of step (i) includes, during at least a portion of the contacting the protein preparation with the solid surface comprising at least one surface-bound ligand capable of binding a metal, contacting the protein preparation with a first component which is a first solid substrate having an electronegative surface, providing a second component which is a second solid substrate having an electropositive surface, contacting the protein preparation with the first and second components, wherein the first and second components are configured such that the protein preparation may contact both components simultaneously, wherein the operating conditions substantially prevent the binding of the desired protein to the first or second components; and separating the desired protein from the first and second components in a conditioned protein preparation.

In some embodiments, the conditioning of the protein preparation of step (i) comprises any combination of the disclosed elements or any portions thereof. In some embodiments where the conditioning of the protein preparation of step (i) may comprise removing particulates such as cells and other residual physical debris created by the cell culture process, such particulates are understood not to constitute the functionalized solids of the disclosed methods.

In some embodiments, the conditioning of the protein preparation of step (i) comprises during at least a portion of step (i) contacting the protein preparation with an undissolved ureide. In certain such embodiments, the undissolved ureide is allantoin. In certain such embodiments, the allantoin is present in a supersaturating amount from about 1% to about 2%, or in a supersaturating amount from about 0.6% to about 6%, or in a supersaturating amount from about 6% to about 10%. In certain such embodiments, the allantoin is present in an amount ranging from 0.6 to 50%, or 0.7 to 25%, or 0.8 to 10%, or 0.9 to 5%, or 1 to 2%, or an intermediate value.

In some embodiments, the soluble electropositive organic additive is selected from the group consisting of ethacridine, chlorhexidine, polyethyleneimine, methylene blue, cetyl trimethyl ammonium bromide, and benzalkonium chloride. In certain such embodiments, the electropositive additive is ethacridine; the ethacridine may be present in a concentration of approximately 0.01% to 0.05%. In certain such embodiments, the electropositive additive is methylene blue; the methylene blue may be present in a concentration of approximately 0.01% to 0.05%. In some embodiments, methylene blue or ethacridine are present at a concentration of 0.020% to 0.025%. In some embodiments, cetyl trimethyl ammonium bromide is present at a concentration of 0.01 to 0.05% or 0.020% to 0.025%.

In some embodiments, the first substrate is particulate. In some embodiments, the second substrate is particulate. In certain such embodiments, the particulate substrate or substrates is each provided as a plurality of particles. In certain such embodiments, the particles of the first substrate, the second substrate or both are non-porous. In others, the particles of the first substrate, the second substrate or both are porous; in certain such embodiments, the pore size of the porous particles is large enough to permit entry of a protein in a protein preparation while in others, the pore size of the porous particles is too small to permit entry of a protein in a protein preparation. In some embodiments, the average pore size of the porous particles is from about 1 nm to about 100 nm. In some embodiments, the particles are sandwiched between porous membranes or monoliths, or the particles are sandwiched between woven or amorphous fibrous filters, or the particles are sandwiched between crystalline frits, or the particles are embedded in a reticular polymer network.

In certain of the preceding embodiments, the protein preparation is contacted with the first and second components by flowing the preparation through the first and second components. Thus, in certain of the preceding embodiments, the protein preparation is contacted with one or more insoluble multivalent organic ions by flowing the preparation through one or more devices that bear the multivalent organic ions on their fluid-contact surface(s).

In certain of the preceding embodiments, the electronegativity of the surface of the first component is conferred through one or more kinds of complex chemical moieties that embody more than one chemical functionality, or through a combination of simple and complex chemical groups mixed on the surface, or a combination of surfaces of differing chemical composition.

In certain of the preceding embodiments, the electronegativity of the surface of the first component is conferred in part by a moiety from the group consisting of iminodiacetic acid, ethylene glycol(aminoethylether)diacetic acid, nitriloacetic acid, aspartic acid, glutamic acid, a carboxylic acid, sulfurous acid, sulfonate, and phosphoric acid.

In certain of the preceding embodiments, the electropositivity of the surface of the second component is conferred through one or more kinds of complex chemical groups that embody more than one chemical functionality, or through a combination of simple and complex chemical groups mixed on the surface, or a combination of surfaces of differing chemical composition.

In certain of the preceding embodiments, the electropositivity of the surface of the second component is conferred in part by a moiety from the group consisting of tris(2-aminoethyl)amine, diethylenetriamine, triethylenetetramine, tetraethylenepentamine, polypropylenimine tetramine, PAMAM dendrimer (ethylenediamine core), deferoxamine, a primary amino group, a secondary amino group, a tertiary amino group, and a quaternary amino group. In certain of the preceding embodiments, the electronegativity of the surface of the first component is conferred in part by iminodiacetic acid and the electropositivity of the surface of the second component is conferred in part by tris(2-aminoethyl)amine. In certain of the preceding embodiments, the first component has a surface-bound chemical moiety possessing metal affinity functionality. In certain of the preceding embodiments, the electropositive surface of the second component includes a surface-bound chemical moiety possessing metal affinity functionality. In certain of the preceding embodiments, at least one of the substrates has one or more chemical moieties in addition to the surface-bound chemical moiety possessing metal affinity functionality wherein such additional chemical moieties enhance the capacity of one or more of the components to participate in hydrogen bonding, hydrophobic interactions, or pi-pi binding with a protein of the protein preparation. In certain such embodiments, the surface-bound chemical moiety possessing metal affinity functionality is a multidentate metal chelating moiety.

In certain of the preceding embodiments, the electropositive surface of the first component includes a surface-bound chemical moiety possessing metal affinity functionality, the electronegative surface of the second component includes a surface-bound chemical moiety possessing metal affinity functionality, and another surface includes a surface-bound chemical moiety possessing an elevated hydrophobic functionality.

In certain of the preceding embodiments, the surface-bound ligand capable of binding a metal provides further chemical functionality selected from the group consisting of electrostatic interactions, hydrophobic interactions, pi-pi interactions, hydrogen bonding, and combinations thereof.

In certain of the preceding embodiments, the contacting the protein preparation with at least one solid surface comprising at least one surface-bound ligand capable of binding a metal of step (i) further comprises contacting the protein preparation with at least one surface-bound ligand that provides a chemical functionality that does not comprise binding a metal. In certain such embodiments, the at least one surface-bound ligand that provides a chemical functionality that does not comprise binding a metal is on the same solid surface as the at least one surface-bound ligand capable of binding a metal; in others, the at least one surface-bound ligand that provides a chemical functionality that does not comprise binding a metal is on a separate solid surface from the at least one surface-bound ligand capable of binding a metal. In certain such embodiments, the chemical functionality that does not comprise binding a metal provides a chemical functionality selected from the group consisting of electrostatic interactions, hydrophobic interactions, pi-pi binding, hydrogen bonding, and combinations thereof.

In certain of the preceding embodiments, the net charge on the surface-bound ligand capable of binding a metal is positive. In certain such embodiments, the surface-bound ligand capable of binding a metal comprises one selected from the group consisting of tris(2-aminoethyl)amine (TREN), diethylenetriamine, triethylenetetramine, tetraethylenepentamine, polypropylenimine tetraamine, deferoxamine (desferrioxamine), histidine, histamine, polyhistidine, and combinations thereof.

In certain of the preceding embodiments, the net charge on the surface-bound ligand capable of binding a metal is negative. In certain such embodiments, the surface-bound ligand capable of binding a metal comprises one selected from the group consisting of iminodiacetic acid (2-(carboxymethylamino)acetic acid), ethylene glycol (aminoethylether) diacetic acid, diethyleaminetriaminepentaacetic acid, nitriloacetic acid (2,2',2"-nitrilotriacetic acid), aspartic acid, glutamic acid, polyaspartic acid, and combinations thereof.

In certain of the preceding embodiments, the at least one solid surface comprises a particle or composite of particles, or a fiber or composite of fibers, or a membrane or composite of membranes, or a monolith or composite of monoliths.

In some embodiments, different surface-bound ligands are present on structurally similar but distinct solid surfaces from the at least one solid surface comprising the at least one surface-bound ligand capable of binding a metal. In some embodiments, different surface-bound ligands are present on structurally distinct solid surfaces from the at least one solid surface comprising the at least one surface-bound ligand capable of binding a metal.

In some embodiments, the conductivity of the protein preparation during step (i) is at a sufficiently high level to substantially avoid precipitation of the desired protein from the sample during step (i). In certain such embodiments, the conductivity of the sample is greater than 20 mS/cm, or the conductivity of the sample is greater than 30 mS/cm, or the conductivity of the sample is greater than about 40 mS/cm, or the conductivity of the sample is greater than about 100 mS/cm, or the conductivity of the sample is at least 5%, 10%, 20%, 50%, 100% or 200% higher than the conductivity sufficient to substantially avoid precipitation of the desired protein during step (i).

In some embodiments, the nonionic organic polymer is selected from the group consisting of glycerol, polyethylene glycol, polypropylene glycol and polybutylene glycol. In certain such embodiments, the nonionic organic polymer is polyethylene glycol with an average molecular weight of between 2 kDA and 12 kDa, or between 4 kDA and 10 kDa, or between 4 kDa and 8 kDa. In some embodiments, the average molecular weight of the polyethylene glycol is about 6 kDa, or 12 kDa, or 10 kDa, or 8 kDa, or 4 kDa, or 2 kDa. In some embodiments, the nonionic organic polymer is polyethylene glycol in an amount that does not cause precipitation of the desired protein before it binds to the affinity chromatography medium. In certain such embodiments, the polyethylene glycol is PEG-6000 at a concentration of no more than a limit selected from the group consisting of 8%, 7%, 6%, and 5%.

In some embodiments, the non-protein-precipitating salt is selected from the group consisting of sodium chloride, potassium chloride, sodium acetate, potassium acetate, sodium thiocyanate, potassium thiocyanate, and guanidine chloride, and combinations thereof. In certain such embodiments, more than one species of non-protein-precipitating salt is present and wherein the aggregate conductivity of the combined non-protein-precipitating salts is in a range of from about 30 mS/cm to about 200 mS/cm. In some embodiments, the non-protein-precipitating salt is sodium chloride with a conductivity ranging from about 50 to 100 mS/cm, or a conductivity ranging from about 30 to 160 mS, or a conductivity greater than 160 mS/cm.

In some embodiments, the affinity chromatography medium comprises a solid material to which is immobilized naturally occurring protein A, recombinant protein A, or a recombinantly derived analog of protein A. In some embodiments, the affinity chromatography medium comprises a solid material to which is immobilized an antibody or fragment thereof with affinity for the desired protein. In others, the affinity chromatography medium comprises a solid material to which is immobilized a bacterial protein or a recombinant variant thereof with an affinity for the desired protein, or a naturally occurring or a synthetic ligand with affinity for the desired protein.

In some embodiments, the affinity chromatography medium is housed in a device suitable for performing chromatography and is in a physical form selected from the group consisting of a monolith, one or a plurality of membranes, one or a plurality particles.

In some embodiments, the desired protein is an antibody or antibody fragment or an Fc-fusion protein. In certain such embodiments, the desired protein is an IgG antibody. In others, the desired protein is a non-IgG antibody. In some embodiments, the desired protein is a recombinant protein.

In some embodiments, the protein preparation is a cell culture harvest, a cell culture supernatant, an antibody-containing solution derived from a cell culture, or an antibody-containing solution from a previous stage of protein purification.

Specific process steps of the integrated conditioning methods disclosed herein are illustrated by the following general example. Cell-containing or cell-free cell culture harvest containing a desired protein such as a species of IgG monoclonal antibody is treated by addition of 1-2% allantoin, then optional subsequent addition of ethacridine, methylene blue, or cetyl trimethyl ammonium bromide at a concentration of 0.02 to 0.03%. The mixture is incubated stirring for 1-2 hours, then electropositive particles with the ability to participate in hydrogen bonding and metal affinity interactions are added to the mixture. In one such embodiment, the electropositive particles are coated with tris(2-aminoethyl)amine (TREN), and are added in an amount ranging from 2% to 5% v/v. Solids are removed by any convenient method, such as centrifugation or membrane filtration. The conditioned liquid may be alternatively or further treated by passage through an electropositively charged chromatography device such as a depth filter. In some embodiments, the protein preparation may be combined at any time, if necessary with a non-precipitating salt such as NaCl in an amount sufficient to prevent the desired protein from being substantially bound to species of organic multivalent ions. In some such embodiments, the desired protein is an IgM monoclonal antibody.

Specific process steps of the integrated conditioning methods disclosed herein are illustrated by the following general example. Cell-containing or cell-free cell culture harvest containing a desired protein such as a species of IgG monoclonal antibody is treated by addition of 1-2% allantoin. The pH is reduced to 5.2. Nonanoic acid is added in an amount of 0.3%. Solids are removed by centrifugation or membrane filtration and the supernatant is exposed to one or more insoluble organic multivalent ions that may also embody or be accompanied by a metal affinity functionality, for example by passing the supernatant through a column or other device containing solid surfaces with those properties. In one such embodiment, electropositive particles with the ability to participate in hydrogen bonding and metal affinity interactions are added to the mixture. In one such embodiment, the electropositive particles are coated with tris(2-aminoethyl)amine (TREN), and are added in an amount ranging from 2% to 5% v/v. The protein preparation may be combined at any time, if necessary with a non-precipitating salt such as NaCl in an amount sufficient to prevent the desired protein from being substantially bound to species of organic multivalent ions.

In one or more of the previous embodiments, the antibody is an IgG. In one such embodiment, the antibody is a monoclonal IgG. In a closely related embodiment, the desired protein comprises an Fc-fragment that is an integral component of a so-called Fc-fusion protein.

In one or more of the previous embodiments, the method is used to purify a non-IgG antibody. In one such embodiment the antibody is an IgM.

In one or more of the previous embodiments, treatment of the unpurified sample with organic multivalent ions particularly involves the addition soluble organic multivalent cations to the sample, and in some embodiments to a final concentration of 0.02 to 0.03%, at a conductivity that substantially prevents the binding of the desired protein to the organic multivalent cations, and optionally in the presence of organic modulators, particularly including allantoin at a supersaturated concentration such as 1-2%.

In one or more of the previous embodiments, treatment of the unpurified sample with organic multivalent ions particularly involves the addition soluble organic multivalent anions to the sample, and in some embodiments to a final concentration of 0.2 to 0.5%, at a conductivity that substantially prevents the binding of the desired protein to the organic multivalent cations, and optionally in the presence of organic modulators, particularly including allantoin at a supersaturated concentration such as 1-2%.

In one or more of the previous embodiments, treatment of the unpurified sample with organic multivalent ions particularly involves its exposure to organic multivalent cations covalently attached to a surface, where the organic multivalent cations may themselves bear or be accompanied by other surfaces that embody other functionalities, particularly including a metal affinity and/or hydrophobic functionality. In some such embodiments, the sample may have been previously treated with an organic modulator, particularly including allantoin at a supersaturation concentration of 1-2%, and/or soluble organic multivalent cations such as ethacridine. In all such embodiments, the salt concentration is adjusted to a level at least sufficient to prevent electrostatic binding of the desired protein to the charged surfaces.

In one or more of the previous embodiments, the protein preparation from which the desired protein is to be purified comprises a cell-containing cell culture harvest.

In one or more of the previous embodiments, the protein preparation from which the desired protein is to be purified comprises a culture harvest from which cells and other physical debris have already been removed.

In one or more of the previous embodiments, at least one stage of the method may additionally include agents intended to inactivate virus, such as tri(n)butyl phosphate, octanoic acid, methylene blue, ethacridine, chlorhexidine, benzalkonium chloride, or related compounds potentially in combination with other agents such as named above, particularly including organic solvents and surfactants.

In one or more of the previous embodiments, the operating pH may be in the range of 5 to 9, or 6 to 8, or 7 to 8, or 5, or 6, or 7, or 8.

In any of the previous embodiments, a chromatography medium of step (ii) may consist of a solid support bearing immobilized naturally occurring protein A, recombinant protein A, or recombinant analogues derived from protein A.

In any of the previous embodiments, a chromatography medium of step (ii) may consist of a solid support bearing positive charges, including so called anion exchangers. In some such embodiments, a solid support bearing positive charges may also bear hydrophobic groups. In other such embodiments, a solid support bearing positive charges may also bear hydrogen bonding residues, or combinations of hydrophobic and hydrogen bonding residues. In other such embodiments, a solid support bearing positive charges may also have the ability to form coordination binds with metal ions.

In any of the previous embodiments, a chromatography medium of step (ii) may consist of a solid support bearing negative charges, including so called cation exchangers. In some such embodiments, a solid support bearing negative charges may also bear hydrophobic groups. In other such embodiments, a solid support bearing negative charges may also bear an integrated metal moiety such as calcium, such as in the case of apatite materials.

In any of the previous embodiments, the chromatography medium of step (ii) may be in the physical form of a monolith, one or a plurality of membranes, one or a plurality particles, or a plurality of magnetic particles, or other physical form, housed in a device suitable for performing chromatography.

Terms are defined so that the methods disclosed may be understood more readily. Additional definitions are set forth throughout the detailed description.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is grown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that must be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety, or immunoconjugates created by synthetic linkage of an IgG to another functional moiety, including another antibody, an enzyme, a fluorophore or other signal generating moiety, biotin, a drug, or other functional moiety.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Electropositive organic additive" refers to an organic molecule, cation or salt of natural or synthetic origin that bears at least one positive charge and may contain multiple positive charges. The electropositive organic additive may also bear negative charges but in such cases will still retain a net positive charge at under the operating conditions where it is employed. Where the electropositive organic additive is net positive it may be provided together with counterions (anions) such as chlorides, bromides, sulfates, organic acids, lactactes, gluconates, and any other anion not incompatible with the method. In some embodiments certain of the positive charges of the electropositive organic additives are supplied by amine, imine or other nitrogen moieties. The electropositive organic additive may additionally include hydrophobic residues, metal affinity residues, hydrogen bonding residues, other functional moieties, and/or it may possess the ability to participate in other types of chemical interactions. Examples of electropositive organic additives in some embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris(2-aminoethyl) amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates); methylene blue, cetyl trimethyl ammonium bromide, chlorhexidine, and benzalkonium chloride.

Anion exchange chromatography" refers to a process employing positive charges covalently bound to a solid surface for the surface of mediating fractionation among sample components of different charge character such that acidic (electronegative) contaminants tend to bind to the positive charges, alkaline (electropositive) contaminants tend to be repelled from the positive charges, and uncharged or electroneutral contaminants tend not to bind the positive charges. Selectivity of such systems is typically controlled by pH and conductivity, where binding typically becomes stronger with increasing pH and/or decreasing salt concentration.

"Anion exchange membrane" or "electropositive membrane" refers to a porous membrane, the surface of which is dominated by positive charge. The membrane pores may range from 5 nm or less to 1 micron or more. Membranes with pores smaller than 200 nm are frequently referred to as ultrafiltration membranes while membranes with pores larger than 200 nm are frequently referred to as microfiltration membranes. Electropositivity may be conferred by chemical groups including but not limited to weak anion exchange groups like amino, ethylene diamino, diethylaminoethyl, polyallylamine, polybenzallylamine, polyethyleneimine; strong anion exchange groups, such as quaternary amino groups; combined weak-strong exchangers, such as polylysine, polyarginine, or Tris(2-aminoethyl)amine, diethylenetriamine, triethylenetetramine, tetraethylenepentamine, polypropylenimine tetraamine, PAMAM dendrimer (ethylenediamine core), or any combinations of the foregoing. Secondary functionalities that create a mixed chemical character on a positively charged membrane may consist of negatively or positively charged groups, hydrophobic groups, pi-pi bonding groups, hydrogen-bonding groups, or metal-chelation groups. The secondary functionalities may exist on the membrane surfaces as an inadvertent byproduct of the manufacturing materials or process by which the particles are synthesized, or they may be present by deliberate design. The concentration of secondary functionalities may range from less than 1milliequivalent per mL of particles, to more than 100 milliequivalents per mL.

"Anion exchange particle" or "electropositive particle" refers to a porous or nonporous particle, the surface of which is dominated by positive charge. Particle size may range from less than 50 nm to more than 200 microns. The particles may comprise a polymeric, crystalline, or ceramic structure, that may also incorporate features that allow them to be sequestered by means that do not involve or interfere with their ability to perform the methods disclosed herein, but may provide some overall enhancement. Examples include but are not limited to features that confer low density that enables flotation, high density that enhances rapid sedimentation, and/or magnetism that enables their collection in a magnetic field. Electropositivity may be conferred by chemical groups including but not limited to weak anion exchange groups like, amino, ethylene diamino, diethylaminoethyl, polyallylamine, polyethyleneimine; strong anion exchange groups, such as quaternary amino groups; combined weak-strong exchangers, such as polylysine, polyarginine, or Tris(2-aminoethyl)amine, diethylenetriamine, triethylenetetramine, tetraethylenepentamine, polypropylenimine tetraamine, PAMAM dendrimer (ethylenediamine core), or any combinations of the foregoing. Secondary functionalities that create a mixed chemical character on a positively charged membrane may consist of negatively or positively charged groups, hydrophobic groups, pi-pi bonding groups, hydrogen-bonding groups, or metal-chelation groups. The secondary functionalities may exist on the membrane surfaces as an inadvertent byproduct of the manufacturing materials or process by which the particles are synthesized, or they may be present by deliberate design. The concentration of secondary functionalities may range from less than 1 milliequivalent per mL of particles, to more than 100 milliequivalents per mL.

"Electropositive surface" refers to a surface of a substrate or solid material which is dominated by positive charge. Electropositivity of a surface may be conferred by chemical groups including but not limited to weak anion exchange groups, like amino, ethylene diamino, diethylaminoethyl; polyallylamine, polyethyleneimine, strong anion exchange groups, such as quaternary amino groups, combined weak-strong exchangers, such as polylysine, polyarginine, or Tris(2-aminoethyl)amine, diethylenetriamine, triethylenetetramine, tetraethylenepentamine, polypropylenimine tetraamine, PAMAM dendrimer (ethylenediamine core), deferoxamine or any combinations of the foregoing. Secondary functionalities that create a mixed chemical character on a positively charged surface may consist of negatively or positively charged groups, hydrophobic groups, pi-pi bonding groups, hydrogen-bonding groups, or metal-chelation groups. The secondary functionalities may exist on electropositive surfaces as an inadvertent byproduct of the manufacturing materials or process by which the particles are synthesized, or they may be present by deliberate design. The concentration of secondary functionalities may range from less than 1milliequivalent per mL of particles, to more than 100 milliequivalents per mL.

"Electronegative surface" refers to a surface of a substrate or solid material which is dominated by negative charge. Electronegativity of a surface may be conferred by chemical groups including but not limited to so called weak cation exchangers, such as carboxyl, aminocarboxyl (iminodiacetic or nitrilloacetic), or phosphoryl or strong exchangers such as sulfo, or sulfate moieties, $SO_3^-$. Secondary functionalities that create a mixed chemical character on a negatively charged surface may consist of negatively or positively charged groups, hydrophobic groups, pi-pi bonding groups, hydrogen-bonding groups, or metal-chelation groups. The secondary functionalities may exist on electronegative surfaces as an inadvertent byproduct of the manufacturing process by which the particles are synthesized, or they may be present by deliberate design. The concentration of secondary functionalities may range from less than 1milliequivalent per mL of particles, to more than 100 milliequivalents per mL.

"Electronegative organic additives" refers to an organic molecule, anion or salt of natural or synthetic origin that bears at least one negative charge and, may contain multiple negative charges. The electronegative organic additive may also bear positive charges but in such cases will still retain a net negative charge at under the operating conditions where it is employed. Where the electronegative organic additive is net negative it may be provided together with counterions (anions) such as potassium, sodium, ammonium, or any other cation not incompatible with the method. In some embodiments certain of the negative charges of the electronegative organic additives are supplied by carboxyl, sulfo, or phsopho moieties. The electronegative organic additive may additionally include hydrophobic residues, metal affinity residues; hydrogen bonding residues, other functional moieties, and/or it may possess the ability to participate in other types of chemical interactions. Examples of negatively charged organic multivalent ions in some embodiments include but are not limited to methyl blue and fatty acids, including heptanoic acid, heptenoic acid, octanoic acid, octenoic acid, nonanoic acid, nonenoic acid, decanoic acid, and salts thereof (e.g. sodium, potassium, ammonium.)

"Ligand" or "surface-bound ligand" refers an assemblage consisting of one or more chemical moieties or functionalities that bind to some other chemical entity. In some embodiments, a ligand is immobilized on a surface with the intent of binding sample (protein preparation) components that contribute to formation or stabilization of aggregate. A ligand may be fairly simple in composition, such as a negative charge, positive charge, or hydrophobic group, or it may be of more complex construction, including two or more distinct components that endow the ligand with the ability to bind chemical entities through interactions that none of the components are individually capable of. In addition, a given ligand may embody abilities to interact with other entities through mechanisms other than its primary or dominant mechanism. For example, the metal affinity ligand iminodiacetic acid contains two carboxyl groups that are negatively charged under most operating conditions, and a nitrogen group that can be positively charged at low pH. In addition to embodying metal affinity, it can also interact with other chemical entities by electrostatic interactions and hydrogen bonding. The metal affinity ligand TREN, when immobilized on a surface, includes 2 primary amines, 1 secondary amine, and 1 tertiary amine. TREN as a whole can form a strong association with a metal dissolved in aqueous solution, while the individual amines can participate in electrostatic and/or hydrogen bonds.

Metal affinity functionality" refers to the capacity of a chemical moiety, which may be immobilized on a surface, to bind metal ions, and in some embodiments, in a 1:1 fashion. Such moieties may have the capacity to form coordination bonds with a metal ion and certain such moieties may be bidentate or multidentate in character. Nonlimiting examples of electronegative moieties with this capability include iminodiacetic acid (2-(carboxymethylamino) acetic acid) and nitrilloacetic acid (2,2',2"-Nitrilotriacetic acid). An example of an electropositive compound with this capability includes but is not limited to Tris(2-aminoethyl)amine or diethylenetriamine, triethylenetetramine, tetraethylenepentamine, polypropylenimine tetraamine, and deferoxamine.

Organic multivalent ion" refers to an organic molecule, ion or salt of natural or synthetic origin that embodies at least one charge and at least one additional chemical functionality, thus rendering it multivalent. An alternative term for characterizing such ions is multimodal organic ions. In some embodiments involving an organic multivalent ion, the at least one additional chemical functionality is an additional charge such that the organic multivalent ion bears two or more like or differing charges. The organic multivalent ion may bear a net positive, net negative, or net neutral charge where neutrality reflects the zwitterionic composition of the organic multivalent ion. Where the organic multivalent ion is net positive it may be provided together with anions such as chlorides, bromides, sulfates, organic acids, lactates, gluconates, and any other anion not incompatible with the method. In some embodiments certain of the positive charges of the organic multivalent ion are supplied by amine, imine or other nitrogen moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in some embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris(2-aminoethyl) amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates.) Where the organic multivalent ion is net negative it may be provided together with cations such, as sodium or potassium, or any other cation not incompatible with the method. In some embodiments certain of the negative charges of the organic multivalent ion are supplied by carboxyl, phospho, or sulfo moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation.

Examples of positively charged organic multivalent ions in some embodiments include but are not limited to ethacridine, methylene blue, cetyl trimethyl ammonium bromide, cationic polymers, and salts thereof (e.g. chlorides, bromides, sulfates, lactates, gluconates). Examples of negatively charged organic multivalent ions in some embodiments include but are not limited to methyl blue and fatty acids, including heptenoic acid, heptenoic acid, octanoic acid, octenoic acid, nonanoic acid, nonenoic acid, decanoic acid, and salts thereof (e.g. sodium, potassium, ammonium.)

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Substrate" or "Solid material" refers to an insoluble organic solid that may be particulate, crystalline, polymeric, fibrous, porous-hollow fibrous, monolithic, membranaceous, in nature. It may consist of non-porous or porous particles, a porous membrane, a porous filter, or a porous monolith. If particulate, the particles may be roughly spherical or not, and may be of sizes ranging from less than 100 nm to more than 100 microns. The average pore size of porous particles may range less than 10 nm (microporous) to more than 100 nm (macroporous). The average pore size in membranes may range from less than 100 nm to more than 1 micron. The average channel size in membranes or monoliths may range from less than 1 micron to more than 10 microns. The solid material may further consist of compound constructions, for example in which particles are embedded in a reticular matrix, sandwiched between membranes, or both.

"Supersaturated ureide" refers to a solution containing an amount of ureide in excess of its maximum solubility under the conditions prevailing in a particular protein preparation. In some embodiments, methods are provided a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize, contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing methods disclosed herein include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPSO (3-[(3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Ureide" refers to a cyclic or acyclic organic molecule of natural or synthetic origin that comprises one or more urea moieties or derivatives thereof. In some embodiments, methods are provided ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In some embodiments, methods are provided organic molecules of the formula R—CO—NH—CO—NH$_2$ or R—CO—NH—CO—NH—CO—R' or R' R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

In some embodiments, a useful starting point in the conditioning of an IgG-containing cell culture harvest, with or without cells, is to add 1% allantoin to a cell-containing or cell-free cell culture supernatant, followed by the addition of methylene blue, or ethacridine, or cetyl trimethyl ammonium bromide at a final concentration of 0.025%. The mixture is incubated stirring for 1-2 hours. Positively charged metal affinity particles such as BioWorks TREN high are equilibrated to roughly physiological conditions, which are generally understood to represent a pH of about 6.8-7.2, and a conductivity of 12 to 17 mS/cm. Equilibrated particles amounting to 2-5% of the sample volume are added to the mixture and incubated stirring for 2-4 hours. The solids are then removed by an expedient manner, such as centrifugation and/or filtration, including depth filtration. Where depth filtration may be used, the depth filter may bear positive charges. In the case of IgG, physiological conductivity is most often sufficient to prevent the loss of IgG through binding to the particles, but it is to be understood that experimentation may be required to determine the minimum conductivity required to prevent such binding. In the case of IgM and other proteins, it may be necessary to substantially elevate the conductivity to prevent losses at any given step of the process. With IgMs it is frequently necessary to increase the conductivity to 20 mS/cm, or 25 mS/cm, by addition of salt. With other protein species it may be necessary to increase conductivity up to 30 mS/cm or higher. Surprisingly, the method works even at conductivity values more than 3 times higher than physiological conductivity, such as about 45 mS/cm. In place of TREN particles, it may be of value to explore particles functionalized with other types of ligands, or combinations of such particles, potentially including examples such as Chelex 100, Macrorep High-S, and Macroprep High-Q. It will be apparent to the person of ordinary skill that a great variety of alternative materials may be used, including custom-synthesized particles, and that the best conditions for a given desired protein will require specific experimentation.

In some embodiments, a useful starting point in the conditioning of an IgG-containing cell culture harvest, with or without cells, is to titrate the pH to 5.2, add 1% allantoin to a cell-containing or cell-free cell culture supernatant, then add nonanoic acid to a final concentration of 0.3%. Experimental results indicated that nonanoic acid is supports the best overall results, but other fatty acids may also be evaluated, such as heptanoic acid at 0.7%, octanoic acid at 0.4%, and decanoic acid at 0.2%. Methyl blue may also be evaluated at 0.5%. The mixture is incubated stirring for 1-2 hours. Positively charged metal affinity particles such as BioWorks TREN high are equilibrated to pH 5.2 and a conductivity of 12 to 17 mS/cm. Equilibrated particles amounting to 2-5% of the sample volume are added to the mixture and incubated stirring for 2-4 hours. Experimental data indicate that an excess of particles reduce the performance of the method, as does an insufficient amount. Best results are most often obtained at about 5%, but amounts as small as 2% may support adequate results. The solids are then removed by an expedient manner, such as centrifugation and/or filtration, including depth filtration. In some embodiments, the particles may be packed in a column and the protein preparation passed through it. Where depth filtration is be used, the depth filter may bear positive charges. In the case of IgG, physiological conductivity is most often sufficient to prevent the loss of IgG through binding to the particles, but it is to be understood that experimentation may be required to determine the minimum conductivity required to prevent such binding. In place of TREN particles, it may be of value to explore particles functionalized with other types of ligands, or combinations of such particles, potentially including examples such as Chelex 100, Macrorep High-S, and Macroprep High-Q. It will be apparent to the person of ordinary skill that a great variety of alternative materials may be used, including custom-synthesized particles, and that the best conditions for a given desired protein will require specific experimentation.

In some embodiments, a useful starting point in the conditioning of an IgG-containing cell culture harvest, is to add electropositive metal affinity particles in an amount of 2-5% of the sample volume, and incubate stirring for 2-4 hours. In such embodiments, the particles should be equilibrated in advance to physiological conditions. In some such embodiments, the disclosed method can be conducted with chromatography marketed for metal affinity chromatography such as BioWorks TREN high. After incubation, the particles are removed by any expedient method, optionally including depth filtration with electropositive filtration media.

In some embodiments, a useful starting point in the conditioning of an IgG-containing cell culture harvest, with or without cells, is to add 1% allantoin to a cell-containing or cell-free cell culture supernatant, then add ethacridine acid to a final concentration of 0.025%. Preliminary experimental results indicated that ethacridine acid is supports the best overall results, but other electropositive organic ions, such as methylene blue and/or cetyl trimethyl ammonium offer valuable utility at the same concentration. The mixture is incubated stirring for 1-2 hours. Positively charged metal affinity particles such as BioWorks TREN high are equilibrated to neutral pH and a conductivity of 12 to 17 mS/cm, alternatively, or optionally in combination with, an electronegative solid substrate comprising hydrophobic moieties on a negatively charged polymer particle, or negatively charged metal chelating moieties on a hydrophobic polymer. Equilibrated particles amounting to 2-5% of the sample volume are added to the mixture and incubated stirring for 2-4 hours. Experimental data indicate that an excess of particles reduce the performance of the method, as does an insufficient amount. Best results are most often obtained at about 5%, but amounts as small as 2% may support adequate results. The solids are then removed by an expedient manner, such as centrifugation and/or filtration, including depth filtration. In some embodiments, the particles may be packed in a column and the protein preparation passed through it. Where depth filtration is be used, the depth filter may bear positive charges. In the case of IgG, physiological conductivity is most often sufficient to prevent the loss of IgG through binding to the particles, but it is to be understood that experimentation may be required to determine the minimum conductivity required to prevent such binding. In place of TREN particles, it may be of value to explore particles functionalized with other types of ligands, or combinations of such particles, potentially including examples such as Chelex 100, Macrorep High-S, and Macroprep High-Q. It will be apparent to the person of ordinary skill that a great variety of alternative materials may be used, including custom-synthesized particles, and that the best conditions for a given desired protein will require specific experimentation.

It will be recognized that because all of the disclosed conditioning methods are directed specifically at reducing the chromatin content of an impure preparation of a desired protein, and because the composition of chromatin is independent of the desired product, and because chromatin derived from dead host cells is a ubiquitous contaminant of cell cultures, that the disclosed methods are applicable to any desired protein produced in any cell culture process. It is noteworthy that even microbial cells contain chromatin analogs that respond to the disclosed methods in the same way as mammalian cells.

It is within the experience of persons of ordinary skill to apply impure preparations conditioned as described above to any of the commonly known adsorptive chromatography methods employed for purification of proteins; including how to select appropriate chromatography media, and how to customize conditions to a particular desired protein.

Since the results obtained by using the methods disclosed herein are a function of chemical processes, it is to be understood that all physical formats are capable of achieving similar results, but may do so with different levels of efficiency, different fluid volumes, and different time intervals. It is within the purview of the person of ordinary skill to determine how to adapt the process to accommodate columns packed with porous particles, or adsorptive membrane units, or monoliths.

EXAMPLES

Example 1

Comparison of conditioning methods. Cell-containing harvest containing about 1.2 g/L of anti-HER2 monoclonal. IgG was conditioned by 3 methods. The first consisted of centrifugation followed by filtration through a 0.22 µm membrane. The second consisted of centrifugation followed by filtration through an anion exchange depth filter. The third consisted of adding 1% allantoin (10 g) to a liter of harvest, followed by the addition of ethacridine to a final concentration of 0.025%. The mixture was incubated stirring for 15 minutes then solids were removed by filtration. Equal proportions of positively charged metal affinity particles (BioWorks TREN hi-sub), negatively charged metal affinity particles (Chelex-100), and positively charged hydrophobic particles (Dowex AG1×2 400-mesh) were combined. 20 mL of the particle mixture was packed into a 1.6×10 cm column, equilibrated to roughly physiological conditions, and the sample passed over the column at a linear flow rate of 300 cm/hr. material conditions by each of the 3 method was applied to a column of immobilized protein A (rAF Protein A Toyopearl 650 M), washed with 1 M NaCl 200 mM histidine, pH 6.7, then eluted with 100 mM arginine, 100 mM acetate, pH 3.7. Host protein contamination in the first sample was 972 ppm of IgG; second, 76 ppm; third, less than 1 ppm.

Example 2

Effects of conditioning method on dynamic binding capacity of protein A. Cell culture supernatant produced by methods 1 and 3 from example 1 were applied to separate protein A columns until IgG was detected in the column effluent. The amount of IgG bound to the column at the point of 5% breakthrough on material conditioned by the first method was about 27.3 mg/mL The corresponding amount of material conditioned by the third method was about 33.7 mg/mL. In a separate experiment using purified IgG to determine the theoretical maximum dynamic binding capacity, 5% breakthrough was detected at 34.0 mg/mL.

Example 3

Effect of different protein A products. Antibody conditioned by method 3 from example 1 was also applied to UNOsphere SuPrA a recombinant protein A, a recombinant protein A, and to a column of MabSelect Sure, a recombinant derivative form of protein A. Whereas the rAF protein A Toyopearl reduced host protein to less than 1 ppm, the MabSelect column reduced it to 7 ppm, and the UNOsphere to 11 ppm.

Example 4

Results from a follow-on polishing purification step. The purified antibody containing less than 1 ppm from example 1 was applied to an anion exchange column of UNOsphere Q, equilibrated with 50 mM Tris, pH 8.2, operated in void exclusion mode. No host proteins were detectable in the purified antibody. A compilation of data from other analytical methods and experiments revealed the following additional results. DNA was reduced by 5 logs at the conditioning step, 3 logs at the protein A step, and 3 logs at the anion exchange step. Minute virus of mice was reduced by 5 logs at the conditioning step, 3.5 logs at the protein A step, and 3.5 logs at the anion exchange step. Murine leukemia virus was reduced by 4 logs at the conditioning step, 4.5 logs at the protein A step, and 4 logs at the anion exchange step. IgG recovery was 99% at the conditioning step, 95% at the protein A step, and 99% at the anion exchange step for a total process recovery of 93%. This highlights another important benefit of the integrated method since IgG yields across other conditioning-protein A-anion exchange processes, are rarely better than 80%.

Example 5

Comparison of adsorption chromatography methods. Cell-free harvest containing 1.5 g/L of anti-HER2 monoclonal IgG was conditions by adding 1% allantoin then reducing the pH to 5.2. Nonanoic acid was added to a final concentration of about 0.4% and incubated stirring for 2 h. Bioworks TREN particles were equilibrated to 50 mM Hepes, 100 mM NaCl, pH 7.0. Settled TREN particles were added to the preparation in an amount of 5% (volume to volume; v:v), and the mixture was incubated stirring for 4 hours. Solids were removed by depth filtration (Sartorius PC1). Host protein contamination was reduced to 485 ppm of IgG, representing greater than 99% reduction from 259,000 ppm in the original harvest. DNA was reduced by 6 logs. A portion of the sample was equilibrated to 50 mM IVIES, pH 6.0 and applied to a cation exchange chromatography column (POROS HXS, Life Technologies) equilibrated to the same conditions, then eluted with an increasing NaCl gradient. Host protein contamination was reduced to less than 1 ppm. Another portion of the sample was applied as-is to a mixed mode hydrophobic cation exchange column (Merck-Millipore HCX) equilibrated to 50 mM phosphate, 100 mM NaCl, pH 7, and eluted with an increasing salt gradient. Host protein contamination was reduced to less than 1 ppm. Another portion of the sample was applied as-is to a protein A affinity chromatography column (AF-rProtein A 650F, Tosoh Bioscience) equilibrated to 50 mM phosphate, 100 mM NaCl, pH 7, and eluted with 100 mM acetic acid, pH 3.5. Host protein contamination was reduced to less than 1 ppm. Another portion of the sample was applied as-is to an anion exchange column of UNOsphere Q (Bio-Rad Laboratories) equilibrated to 50 mM Tris, pH 8.2, and operated in void exclusion mode (Nian et al, supra), Tosoh Bioscience). Host protein contamination in the void fraction was reduced to 6 ppm.

Example 6

An IgG-containing cell culture harvest containing 259,218 ppm host protein contaminants and 21% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 308 ppm and aggregates to less than 0.05%. The tangential flow filtration subunit was set up with a polyethersulfone (PES) membrane with an average pore size corresponding to a hypothetical globular protein with a hydrodynamic diameter of 50 kDa (Millipore). A single adsorption chromatography subunit was set up with a strong anion exchange monolith (CIM QA, BIA Separations). The conditioned harvest was concentrated to about 20 mg/mL through the ultrafiltration subunit with the adsorption chromatography unit off-line. The adsorption chromatography subunit was put in line with the tangential flow filtration subunit, and the buffer was exchanged to 50 mM Tris, pH 8.0. When the buffer flowing through the system reached the same pH and conductivity as the input buffer, the adsorption chromatography subunit line was rinsed, and the IgG collected. Aggregates were reduced to less than 0.01% and host proteins were reduced to 11 ppm.

Example 7

The conditioned harvest of Example 6 was applied to a system with the same tangential flow filtration subunit, but the adsorption chromatography subunit was replaced with a Sartobind Phenyl membrane adsorber (Sartorius). The conditioned harvest was concentrated to about 20 mg/mL with no adsorption chromatography units in line. The phenyl adsorption chromatography subunit was put in line and the buffer exchanged to 50 mM HEPES, 1.7 M NaCl, pH 7.0. When the buffer flowing through the system reached the same pH and conductivity as the input buffer, the phenyl adsorption chromatography subunit line was rinsed, and the IgG collected. Aggregates were reduced to less than 0.01% and host proteins were reduced to 9 ppm.

Example 8

The conditioned harvest of Example 6 was applied to a system with the same tangential flow filtration subunit, and the same adsorption chromatography subunit, but an additional adsorption chromatography subunit in the form of a Sartobind Phenyl membrane adsorber (Sartorius). The conditioned harvest was concentrated to about 20 mg/mL with no adsorption chromatography units in line. The phenyl adsorption chromatography subunit was put in line and the buffer exchanged to 50 mM HEPES, 1.7 M NaCl, pH 7.0. When the buffer flowing through the system reached the same pH and conductivity as the input buffer; the phenyl adsorption chromatography subunit line was rinsed, and switched off-line at the same time the QA monolith adsorption chromatography subunit was put on line. The buffer was exchanged to 50 mM Tris, pH 8.0. When the buffer flowing through the system reached the same pH and conductivity as the input buffer, the QA monolith adsorption chromatography subunit line was rinsed, and the IgG collected. Aggregates were reduced to less than 0.01% and host proteins were reduced to 1 ppm.

Example 9

The experiment of Example 8 was conducted with the same materials and conditions, except substituting different anion exchange adsorption chromatography units in place of the QA monolith. Substitution of a Sartobind Q membrane adsorber (Sartorius) resulted in reduction of host protein to 1 ppm. Substitution of a salt tolerant interaction chromatography membrane adsorber (Sartorius) resulted in reduction of host protein to 1 ppm. Substitution of a DEAE (BIA Separations) resulted in reduction of host protein to 1 ppm. Substitution of an EDA monolith (BIA Separations) resulted in reduction of host protein to 1 ppm. Aggregate levels were reduced to less than 0.01% in all experiments.

Example 10

The experimental format of Example 8 was reproduced except setting up the tangential flow filtration subunit with a cellulose membrane with a membrane with an average pore size corresponding to a hypothetical globular protein with a hydrodynamic diameter of 30 kDa (Millipore). The phenyl adsorption chromatography subunit was the same. Host protein contamination in the purified IgG was reduced to 2 ppm. Aggregates were less than 0.01%.

Example 11

The experimental framework of Example 9 was reproduced except including a second adsorption chromatography subunit in the form of an EDA monolith. The system was run as in example 9. Host protein was undetectable. Aggregates were less than 0.01%.

Example 12

An IgG-containing cell culture harvest containing 243,997 ppm host protein contaminants and 24% aggregates was conditioned by addition of 1% allantoin, 0.4% caprylic acid, pH 5.2; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 305 ppm and aggregates to less than 0.05%. The antibody was further purified by cation exchange chromatography, reducing the host protein to 5 ppm, which was applied to a version of the disclosed apparatus with the tangential flow filtration subunit with a cellulose membrane with an average pore size corresponding to a hypothetical globular protein with a hydrodynamic diameter of 30 kDa (Millipore), and a single adsorption chromatography subunit with a strong anion exchange monolith (CIM QA, BIA Separations). Host protein was undetectable. Aggregates were less than 0.01%.

Example 13

An IgG-containing cell culture harvest containing 243,997 ppm host protein contaminants and 24% aggregates was conditioned by addition of 1% allantoin, 0.4% caprylic acid, pH 5.6; incubated for 2 hours, following which electropositive metal affinity particles (TREN 40 high, Bio-Works) were added in an amount of 4%, and incubated mixing for an additional 4 hours, then solids were removed through an electropositive depth filter (Sartorius PC1). Host proteins were reduced to 3,551 ppm and aggregates to less than 0.5%. The antibody was further purified by precipitation with 1.8 M ammonium sulphate, reducing the host protein to 1,423 ppm, which was applied to a version of the disclosed apparatus with the tangential flow filtration subunit with a PES membrane with an average pore size corresponding to a hypothetical globular protein with a hydrodynamic diameter of 50 kDa (Millipore), and a single adsorption chromatography subunit with a strong anion exchange monolith (CIM QA, BIA Separations). Host protein was undetectable was reduced to 12 ppm. Aggregates were less than 0.05%.

Example 14

1 L of cell culture harvest containing about 1 g/L of an IgG monoclonal antibody specific for HER2 antigen was treated with 1% allantoin. Conductivity was about 13 mS/cm and pH was about 6.8. The additives had the effect of accelerating sedimentation. Solid materials were removed by filtration, leaving a sparking clear antibody-containing filtrate. Antibody recovery was 99%. 20 mL of BioWorks TREN hi-sub, an agarose porous particle-based electropositive metal affinity material was packed in a column (1.6×10 cm) and equilibrated to 50 mM Hepes, 150 mM NaCl, pH 7.0. The clarified filtrate was passed through the column at a linear flow rate of 200 cm/hr. The original harvest contained more than 20% aggregates, particularly containing at least 10% so-called high molecular weight aggregates. The treated sample contained less than 0.05% high molecular weight aggregates and less than 4% total aggegates. DNA as measure by fluorescent dye assay was reduced by greater than 98%, but qPCR indicated that reduction was actually greater than 99.999%. Histone proteins were reduced by at least 98% and general host protein levels, as measured by Cygnus ELISA was reduced by 62%. Antibody recover was 99%.

Example 15

The procedure of example 14 was repeated except substituting TREN for a 1:1 mixture of TREN plus Dowex AG1×2, a hydrophobic electropositive particulate material. All results were nominally the same, except that antibody recovery was reduced to 95% and analytical size exclusion chromatography showed that two strongly hydrophobic contaminants evident after Example 15, were eliminated.

It will be apparent to a person of skill in the art that the methods can be applied with valuable benefits to any affinity chromatography method and any desired protein that can be purified by an affinity chromatography method. Techniques suited to the methods particularly include those with the word affinity in their name, such as immunoaffinity, biological affinity, bioaffinity, pseudobioaffinity, and biomimetic affinity.

The methods disclosed herein may be combined with other purification methods to achieve higher levels of purification. Examples of such other purification methods include, but are not limited to other methods commonly used for purification of proteins, such as anion exchange chromatography, cation exchange chromatography, hydrophobic interaction chromatography, immobilized metal affinity chromatography, and additional mixed mode chromatography methods. It is within the purview of a person of ordinary skill in the art to develop appropriate conditions for the various methods and integrate them with the methods disclosed herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the methods disclosed herein.

Many modifications and variations of methods disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the methods disclosed herein being indicated by the following claims.

What is claimed is:

1. A method for the purification of at least one desired protein from a protein preparation comprising the steps of (a) conditioning an impure protein preparation by contacting it with (i) at least one species of soluble or insoluble electropositive organic additive selected from methylene blue, ethacridine, chlorhexidine, benzalkonium chloride, cetyl trimethyl ammonium bromide, Tris(2-aminoethyl) amine (TREN), and a derivative of TREN, and (ii) at least one electronegative organic additive selected from the group consisting of nonanoic acid, nonenoic acid, heptanoic acid, heptenoic acid, octanoic acid, octenoic acid, decanoic acid and methyl blue; (b) subsequently removing solids with the result of removing at least 95% of chromatin from the protein preparation, thereby providing a conditioned protein preparation comprising the at least one desired protein; and (c) applying the conditioned protein preparation, optionally after a buffer exchange step, to an adsorptive chromatography medium for purification of the desired protein.

2. The method of claim 1, wherein the electropositive organic additive comprises methylene blue or ethacridine.

3. The method of claim 1, wherein the electropositive organic additive is present at a concentration of 0.001% to 2%, 0.005% to 1%, 0.01% to 0.05% or 0.020% to 0.025%.

4. The method of claim 1, wherein the electropositive organic additive comprises Tris(2-aminoethyl) amine.

5. The method of claim 1, wherein the electronegative organic additive is affixed to an insoluble surface.

6. The method of claim 1, wherein the electronegative organic additive is present at a concentration of 0.05% to 5%, 0.1% to 1%, or 0.20% to 0.5%.

7. The method of claim 1, wherein step (a) comprises contacting the protein preparation with allantoin at a concentration range selected from the group consisting of 0.6 to 50%, 0.7 to 20%, 0.8 to 10%, 0.9 to 5%, and 1 to 2%.

8. The method of claim 1, wherein step (a) is performed under conditions that substantially prevent the precipitation of the desired protein.

9. The method of claim 1, wherein removal of solids in step (b) is accomplished by centrifugation or filtration.

10. The method of claim 1, wherein the adsorbent chromatography medium comprises a monolith, a membrane, a plurality of fluidized particles, or a plurality of particles packed in a column.

11. The method of claim 1, wherein the adsorbent chromatography medium comprises one or more mediums selected from the group consisting of a biological affinity chromatography medium, a protein A affinity chromatography medium, a synthetic affinity chromatography medium, a cation exchange chromatography medium, an anion exchange chromatography medium, a hydrophobic interaction chromatography medium, and a multimodal chromatography medium.

12. The method of claim 1, wherein the impure preparation containing the desired protein is a cell culture harvest, optionally cell-free or containing cells.

* * * * *